(12) United States Patent
Stolarik et al.

(10) Patent No.: US 10,342,647 B2
(45) Date of Patent: Jul. 9, 2019

(54) APPARATUS AND METHOD FOR REMOVING AMALGAM AND WASTE PARTICLES FROM DENTAL OFFICE SUCTION EFFLUENT

(71) Applicant: Crosstex International, Inc., Hauppauge, NY (US)

(72) Inventors: Douglas S. Stolarik, Mentor, OH (US); Douglas M. Horner, Gates Mills, OH (US); Michael P. Mormino, Aurora, OH (US); Owen E. Boyd, Holliston, MA (US)

(73) Assignee: Crosstex International, Inc., Hauppauge, NY (US)

( * ) Notice: Subject to any disclaimer, the term of this patent is extended or adjusted under 35 U.S.C. 154(b) by 12 days.

(21) Appl. No.: 15/239,214

(22) Filed: Aug. 17, 2016

(65) Prior Publication Data

US 2018/0289457 A1    Oct. 11, 2018

Related U.S. Application Data

(63) Continuation of application No. 14/519,959, filed on Oct. 21, 2014, now abandoned.
(Continued)

(51) Int. Cl.
*A47L 5/38* (2006.01)
*C02F 1/28* (2006.01)
(Continued)

(52) U.S. Cl.
CPC ................. *A61C 17/046* (2013.01)

(58) Field of Classification Search
CPC ...... A47L 7/0019; A47L 7/0047; A47L 9/185; A47L 7/0028; A47L 5/38; A47L 9/1608;
(Continued)

(56) References Cited

U.S. PATENT DOCUMENTS

| 3,665,682 A | * | 5/1972 | Ciavattoni | ........... A61C 17/046 |
| | | | | 55/337 |
| 3,870,486 A | * | 3/1975 | Eriksson | ............... A47L 7/0019 |
| | | | | 55/309 |

(Continued)

OTHER PUBLICATIONS

SolmeteX Hg5® Amalgam Separator, Type 2—Maximum Flow=1000 ml/min, Installation and Maintenance Instructions, Rev—Apr. 27, 2017 (8 pages).
(Continued)

*Primary Examiner* — Amber R Orlando
*Assistant Examiner* — Minh Chau T Pham

(57) ABSTRACT

An apparatus and method for removing amalgam and waste particles from dental office suction effluent. The apparatus includes an upper chamber and a solids collection canister removably secured thereto. Dental office suction effluent drawn through a dental suction wand enters the upper chamber along a lateral flow path above a substantially cylindrical internal wall portion. A gas component of dental office suction effluent changes direction by more than 60° before it exits the upper chamber through an exit port. A riser conveys a liquid and solids component of dental office suction effluent through a drain into the solids collection canister. A flow restrictor allows liquids and gases to exit the solids collection canister interior volume but prohibits solids from exiting the solids collection canister interior volume.

21 Claims, 12 Drawing Sheets

Related U.S. Application Data

(60) Provisional application No. 62/013,019, filed on Jun. 17, 2014, provisional application No. 61/893,933, filed on Oct. 22, 2013.

(51) Int. Cl.
*C02F 1/20* (2006.01)
*A61C 17/06* (2006.01)

(58) Field of Classification Search
CPC ... A47L 9/1641; A61C 1/0007; B01D 47/021; C02F 1/28; C02F 1/20
USPC .......... 55/309, 426, DIG. 3, DIG. 8; 15/314, 15/347, 352, 353; 137/883; 451/453; 210/188, 232, 265, 282, 295, 502.1, 914
See application file for complete search history.

(56) References Cited

U.S. PATENT DOCUMENTS

| | | | |
|---|---|---|---|
| 3,988,134 A * | 10/1976 | Gandrud | A61C 1/0007 137/550 |
| 4,083,705 A * | 4/1978 | Parise | A47L 7/0019 15/353 |
| 4,226,054 A * | 10/1980 | Coty | A47L 7/0047 451/453 |
| 5,343,592 A * | 9/1994 | Parise | A47L 9/181 15/353 |
| 5,421,996 A | 6/1995 | Trawöger et al. | |
| 5,741,134 A | 4/1998 | Davis | |
| 5,743,735 A | 4/1998 | Vollstedt | |
| 5,958,113 A * | 9/1999 | Collins | A47L 7/0028 15/353 |
| 6,083,307 A * | 7/2000 | Dular | B01D 47/021 15/353 |
| 6,409,803 B1 | 6/2002 | Tremel et al. | |
| 6,592,754 B2 | 7/2003 | Chilibeck | |
| 6,638,066 B2 | 10/2003 | Hubner et al. | |
| 6,660,160 B1 | 12/2003 | Ernryd | |
| 6,692,636 B2 | 1/2004 | Chilbeck | |
| 6,790,038 B2 | 9/2004 | Hubner et al. | |
| 6,797,178 B2 | 9/2004 | Albiston et al. | |
| 6,946,069 B2 | 9/2005 | Chilibeck | |
| 7,063,793 B2 | 6/2006 | Albiston et al. | |
| 7,080,425 B2 * | 7/2006 | Smith | A47L 5/38 15/314 |
| 7,131,839 B2 | 11/2006 | March | |
| 7,166,214 B2 | 12/2007 | Armstrong et al. | |
| 7,306,460 B2 | 12/2007 | Hubner et al. | |
| 7,422,615 B2 * | 9/2008 | Kim | A47L 9/1608 55/426 |
| 7,604,674 B2 * | 10/2009 | Han | A47L 9/1641 15/347 |
| 7,753,976 B2 * | 7/2010 | Hyun | A47L 9/1608 15/352 |
| 7,767,079 B2 | 8/2010 | Darcy et al. | |

OTHER PUBLICATIONS

Final Draft—ISO Standard 11143, Dentistry—Amalgam separators, 2008 (33 pages) (extraneous markings of unknown origin added).

* cited by examiner

APPARATUS AND METHOD FOR REMOVING AMALGAM AND WASTE PARTICLES FROM DENTAL OFFICE SUCTION EFFLUENT

This application is a continuation of U.S. application Ser. No. 14/519,959, filed Oct. 21, 2014, now abandoned, and claims priority to U.S. Prov. Patent App. Ser. No. 61/893,933, filed on Oct. 22, 2013, and US Prov. Patent App. Ser. No. 62/013,019, filed on Jun. 17, 2014, both of which are incorporated herein in their entirety.

BACKGROUND OF INVENTION

The present invention relates to an apparatus and a method for removing amalgam and waste particles from dental office suction effluent.

In dentistry and in the present specification, the term "amalgam" generally refers to the alloys of mercury and other metals such as silver, tin, copper, which are used to form dental restorative materials (e.g., fillings). Amalgam was the restorative material of choice for many years due to its relatively low cost, ease of application, strength and durability. However, it has become less popular due to concerns over the toxicity of mercury, which is the major component of amalgam, the development of alternative materials that are more aesthetically pleasing, and also due to concerns over environmental pollution.

Although amalgam is less frequently used for new dental fillings than was the case some decades ago, amalgam nevertheless continues to comprise a significant portion of the metallic particle component of dental office effluent. This is the case because when old fillings comprising amalgam are drilled out and removed, amalgam particles are evacuated from the mouth as waste in such effluent. Furthermore, amalgam continues to be preferred for some tooth filling applications.

In addition to amalgam, dental office suction effluent includes saliva, rinsing fluid and solid particles such as aluminum oxides, which are used in abrasion treatments. It is important that the solid components of dental office suction effluent be separated from the liquid wastes before the latter are discharged into sanitary treatment systems.

The International Organization for Standardization (hereinafter "ISO") has adopted a standard, which specifies the efficiency of amalgam separators in terms of the level of retention of amalgam based on a laboratory test (ISO 11143:2008). And there are many amalgam separators available that comply with such standard.

One amalgam separator known in the art is sold by SolmeteX, Inc. of Northborough, Mass. under the trade designation HG5®. This device consists of an upper chamber having two openings in an upper end and two openings in a lower end. One of the openings in the upper end is in fluid communication with a vacuum pump via piping, and the other opening in the upper end is in fluid communication with a dental suction wand. A collection chamber is removably connected to the lower end of the upper chamber. Waste is drawn into the upper chamber through the dental suction wand with air drawn into the upper chamber by the vacuum pump. Liquids and solids in the dental suction effluent stream are separated from the air to some degree in the upper chamber. The air flows out of the upper chamber to the vacuum pump. The liquids and solids flow under the force of gravity through one of the openings in the lower end of the upper chamber and then through straight tubing into the collection chamber. Solid particles settle and accumulate in the bottom of the collection chamber. Liquid waste is drawn up through a filter that extends into the collection chamber from the second opening in the lower end of the upper chamber. This opening is in fluid communication with a bypass conduit, which is connected to the piping to the vacuum pump. While the SolmeteX HG5® amalgam separator, and other similar products, are capable of separating amalgam and other solid particles from dental waste effluent streams, there is substantial room for improvement in terms of collection capacity, separation efficiency and ease of use.

BRIEF SUMMARY OF THE INVENTION

In view of the foregoing, the present invention is directed toward an apparatus and method for removing amalgam and waste particles from dental office suction effluent. The apparatus includes an upper chamber and a solids collection canister removably secured thereto. Dental office suction effluent drawn through a dental suction wand enters the upper chamber along a lateral flow path above a substantially cylindrical internal wall portion. A gas component of dental office suction effluent changes direction by more than 60° before it exits the upper chamber through an exit port. A riser conveys a liquid and solids component of dental office suction effluent through a drain into the solids collection canister. A flow restrictor allows liquids and gases to exit the solids collection canister interior volume but prohibits solids from exiting the solids collection canister interior volume.

According to one aspect, an apparatus for removing amalgam and waste particles from dental office suction effluent comprises an upper chamber having an upper end and a lower end, and a solids collection canister removably secured to the lower end of the upper chamber. The upper chamber includes an upper portion, a central portion having a substantially cylindrical internal wall portion, and a lower portion having a basin portion. The upper portion, the central portion and the basin portion of the lower portion cooperate to define an upper chamber interior volume. An inlet provided in the upper portion of the upper chamber establishes a connection to an inlet line in fluid communication with at least one dental suction wand. An outlet provided in the lower portion of the upper chamber establishes a connection to an outlet line in fluid communication with a vacuum pump. The solids collection canister includes a top portion and a bottom portion which together define a solids collection canister interior volume. The top portion of the solids collection canister is provided with a first opening and a second opening. The first opening communicates with a drain provided in the basin portion of the upper chamber, and the second opening communicates with the outlet. A riser communicates with the first opening. The riser is adapted to convey liquids and solids of the dental office suction effluent flowing from the upper chamber interior volume through the drain and the first opening to the bottom portion of the solids collection canister. A flow restrictor communicates with the second opening. The flow restrictor is adapted to allow liquids and gases of the dental office suction effluent to exit the solids collection canister interior volume but prohibit solids of the dental office suction effluent from exiting the solids collection canister interior volume.

According to another aspect, an apparatus for removing amalgam and waste particles from dental office suction effluent comprises an upper chamber having an upper end, a lower end and a basin portion. The upper chamber defines a longitudinal axis. A solids collection canister removably secured to the lower end of the upper chamber. The solids collection canister includes a top portion provided with a first opening and a second opening. The first opening communicates with a drain provided in the basin portion of the upper chamber. An inlet is provided in the upper chamber for establishing a connection to an inlet line in fluid communication with at least one dental suction wand. The inlet is shaped and configured such that dental office suction effluent enters the upper chamber along a lateral flow path which is substantially perpendicular to the longitudinal axis of the upper chamber. An outlet is provided in the upper chamber for establishing a connection to an outlet line in fluid communication with a vacuum pump. An exit port is provided in the upper chamber and communicates with the outlet. The exit port discharges gases of dental office suction effluent entering the upper chamber through the inlet. A separate gas conduit is provided in the upper chamber and has a longitudinal axis substantially parallel to the longitudinal axis of the upper chamber. The gas conduit communicates with the exit port and the outlet for directing the discharged gases toward the outlet. A flow restrictor is located in the solids collection canister. The flow restrictor is adapted to allow liquids and gases of the dental office suction effluent to exit the solids collection canister but prohibit at least about 99% by weight of solids of the dental office suction effluent that enter the solid collection canister from exiting the solids collection canister.

According to yet another aspect, a method for removing amalgam and waste particles from dental office suction effluent comprises imparting a circular flow path to a dental office suction effluent entering an upper separation chamber of a separation apparatus; separating gases from the dental office suction effluent and discharging the separated gases from the upper separation chamber; directing the dental office suction effluent into a solids collection canister removably secured to a lower end of the upper chamber via a riser located in the solids collection canister; separating solids from the dental office suction effluent in the solids collection canister; and discharging liquids and gases of the dental office suction effluent through a flow restrictor located in the solids collection canister.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
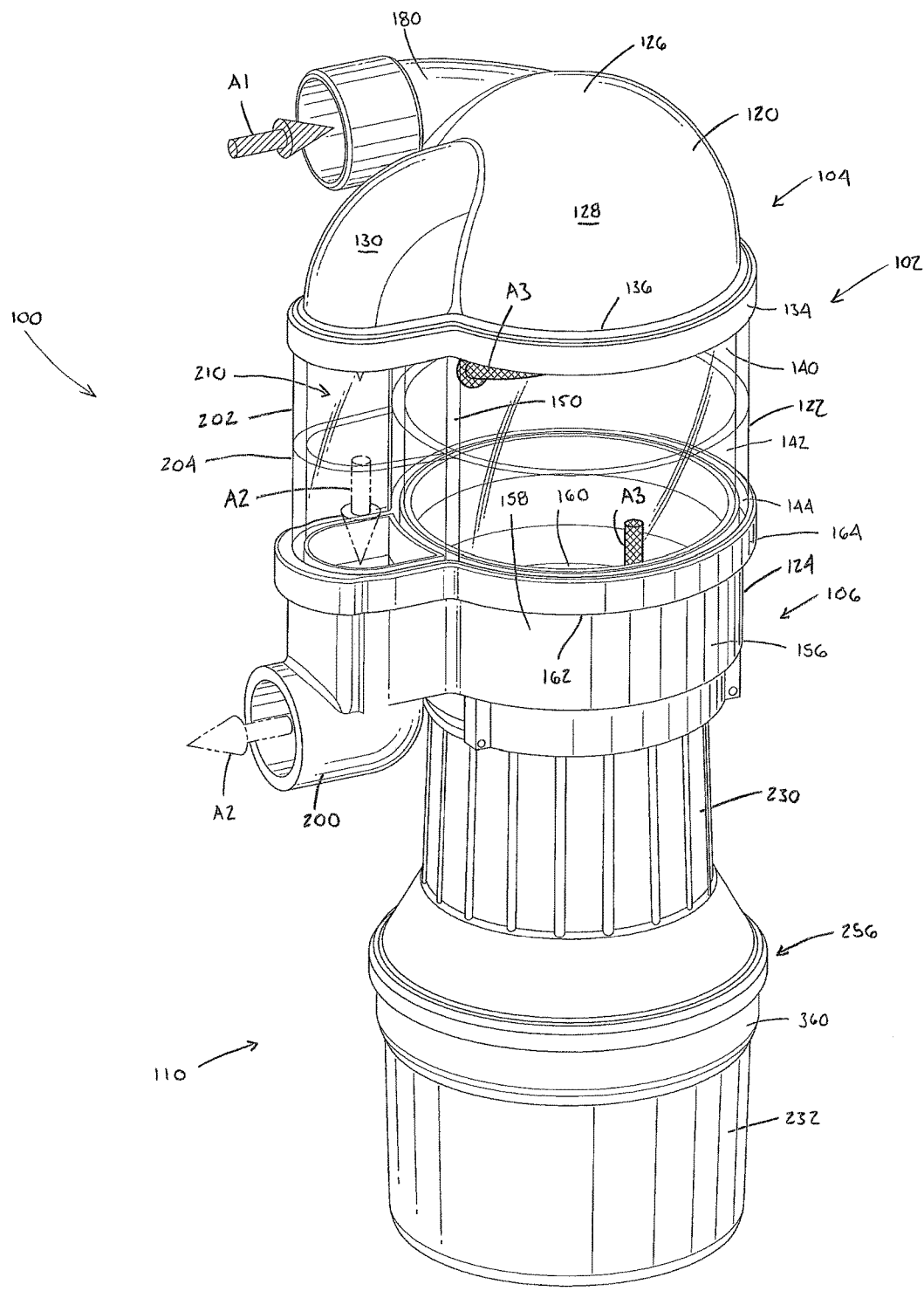
FIG. 1 is a perspective view of one embodiment of an apparatus for removing amalgam and waste particles from dental office suction effluent according to the present invention.

It should, of course, be understood that the description and drawings herein are merely illustrative and that various modifications and changes can be made in the structures disclosed without departing from the present disclosure. In general, the figures of the exemplary apparatus for removing amalgam and waste particles from dental office suction effluent are not to scale. It should be appreciated that the term "plurality" means "two or more", unless expressly specified otherwise. It will also be appreciated that the various identified components of the exemplary apparatus disclosed herein are merely terms of art that may vary from one manufacturer to another and should not be deemed to limit the present disclosure.

FIGS. 1-5 illustrate one embodiment of an apparatus 100 for removing amalgam and waste particles from dental office suction effluent according to the present invention. The apparatus 100 generally comprises an upper chamber 102 having an upper end 104 and a lower end 106, and a solids collection canister 110 removably secured to the lower end 106 of the upper chamber 102. The upper chamber 102 includes an upper portion 120, a central portion 122 and a lower portion 124. The upper portion 120 includes an outer wall portion 126 having a first wall portion 128 and a second wall portion 130 projecting outwardly from the first wall portion 128. According to one aspect, the first wall portion 128 can be substantially hemispherical dome-shaped; although, this is not required. A flange 134 extends about a periphery 136 of the outer wall 126. The flange 134 is shaped and configured to receive an upper part 140 of the central portion 122, thereby securing the upper portion 120 to the central portion 122. It should be appreciated that the connection between the flange 134 of the upper portion 120 and the central portion 122 can be in the form of a sealed interference fit allowing for the removal of the upper portion 120 from the apparatus 100. In the alternative, the connection between the flange 134 of the upper portion 120 and the central portion 122 can be in the form of a permanent connection via, for example, an adhesive and/or welding.

The central portion 122 includes an outer wall 142 defined by the upper part 140 and a lower part 144. The upper and lower parts 140, 142 of the central portion 122 together define a substantially cylindrical internal wall portion 150, which in the depicted embodiment in an inner wall portion of the outer wall 142. The inner wall portion 150 is adapted to impart a circular flow to the dental office suction effluent being drawn into the upper chamber 102. The lower portion 124 of the upper chamber 102 includes a basin portion 156 defined by an outer wall 158 and a bottom wall 160. Located about a periphery of an upper part 162 of the outer wall 158 is a flange 164 shaped and configured to receive the lower part 144 of the central portion 122, thereby securing the lower portion 124 to the central portion 122. Again, it should be appreciated that the connection between the flange 164 of the lower portion 124 and the central portion 122 can be in the form of a sealed interference fit allowing for the removal of the basin portion 156 from the apparatus 100. In the alternative, the connection between the flange 164 of the lower portion 124 and the central portion 122 can be in the form of a permanent connection via, for example, an adhesive and/or welding. As better illustrated in FIG. 3, the upper portion 120, the outer wall 142 (i.e., the substantially cylindrical internal wall portion 150) of the central portion 122 and the basin portion 156 of the lower portion 124 cooperate to define an upper chamber interior volume 170.

An inlet 180 is provided in the upper portion 120 of the upper chamber 102 for establishing a connection to an inlet line (not shown) in fluid communication with at least one dental suction wand (not shown). The inlet 180 is configured such that dental office suction effluent drawn through the at least one dental suction wand enters the upper portion 120 of the upper chamber 102 along an initial lateral flow path into the upper portion 120 and then a circular flow path through the upper portion 120 above the internal wall portion 150 of the central portion 122 (the lateral/circular flow path shown by arrows "A1" in FIGS. 1-3). The term "lateral" as used herein means that the flow path is substantially sideways or horizontal (i.e., perpendicular) relative to a longitudinal axis defined by the upper chamber 102, and the term "circular" as used herein mean a flow path substantially around the longitudinal axis of the upper chamber 102. It should be appreciated that the use of the substantially hemispherical domed-shaped first wall portion 128 of the upper portion outer wall 126 allows the incoming dental office suction effluent to quickly change direction as it enters the upper portion 120 of the apparatus 100.

Figure 2:
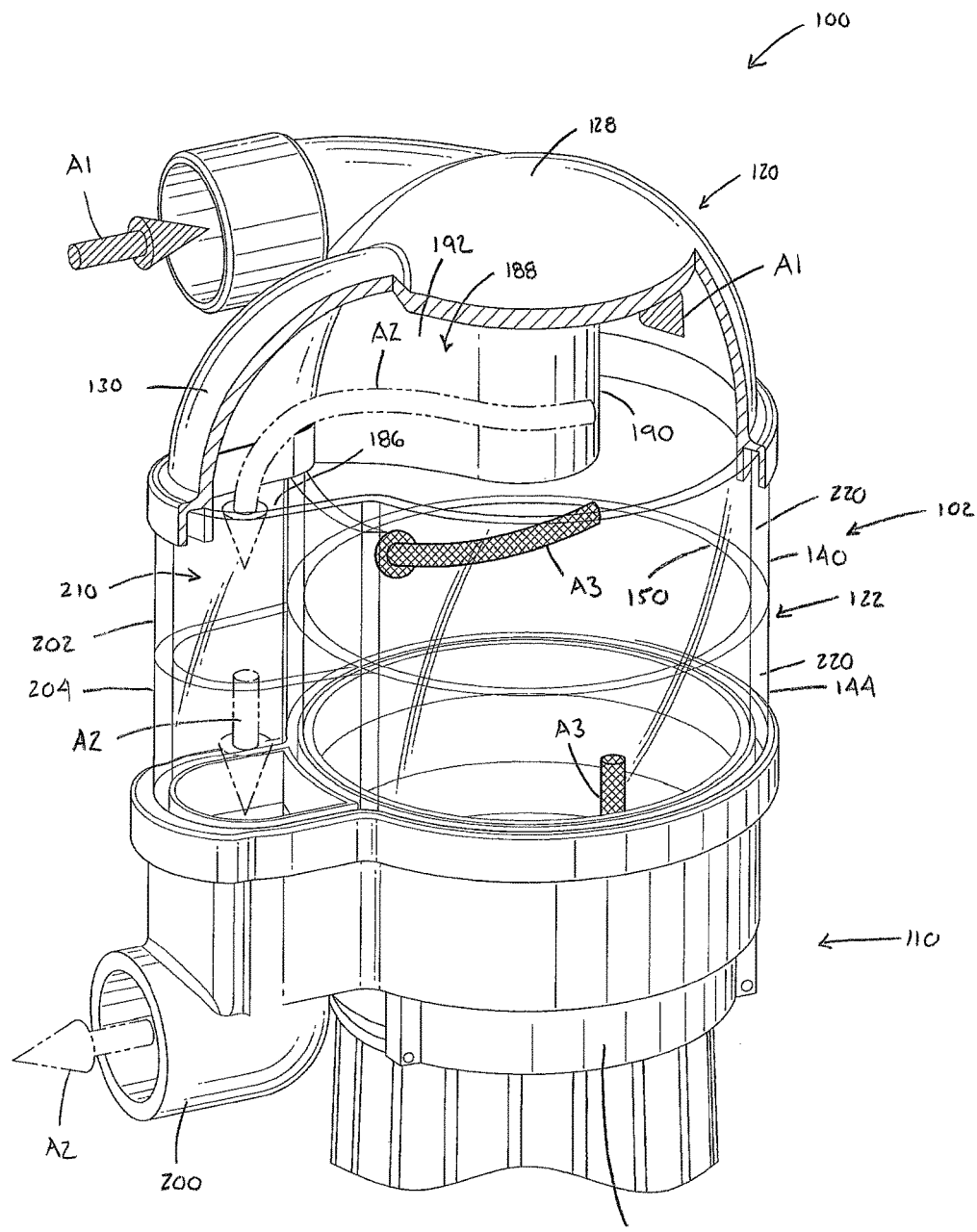
FIG. 2 is a partial section view of the upper portion of the apparatus shown in FIG. 1, which shows the primary flow path of dental office suction effluent drawn into the apparatus.
Figure 3:
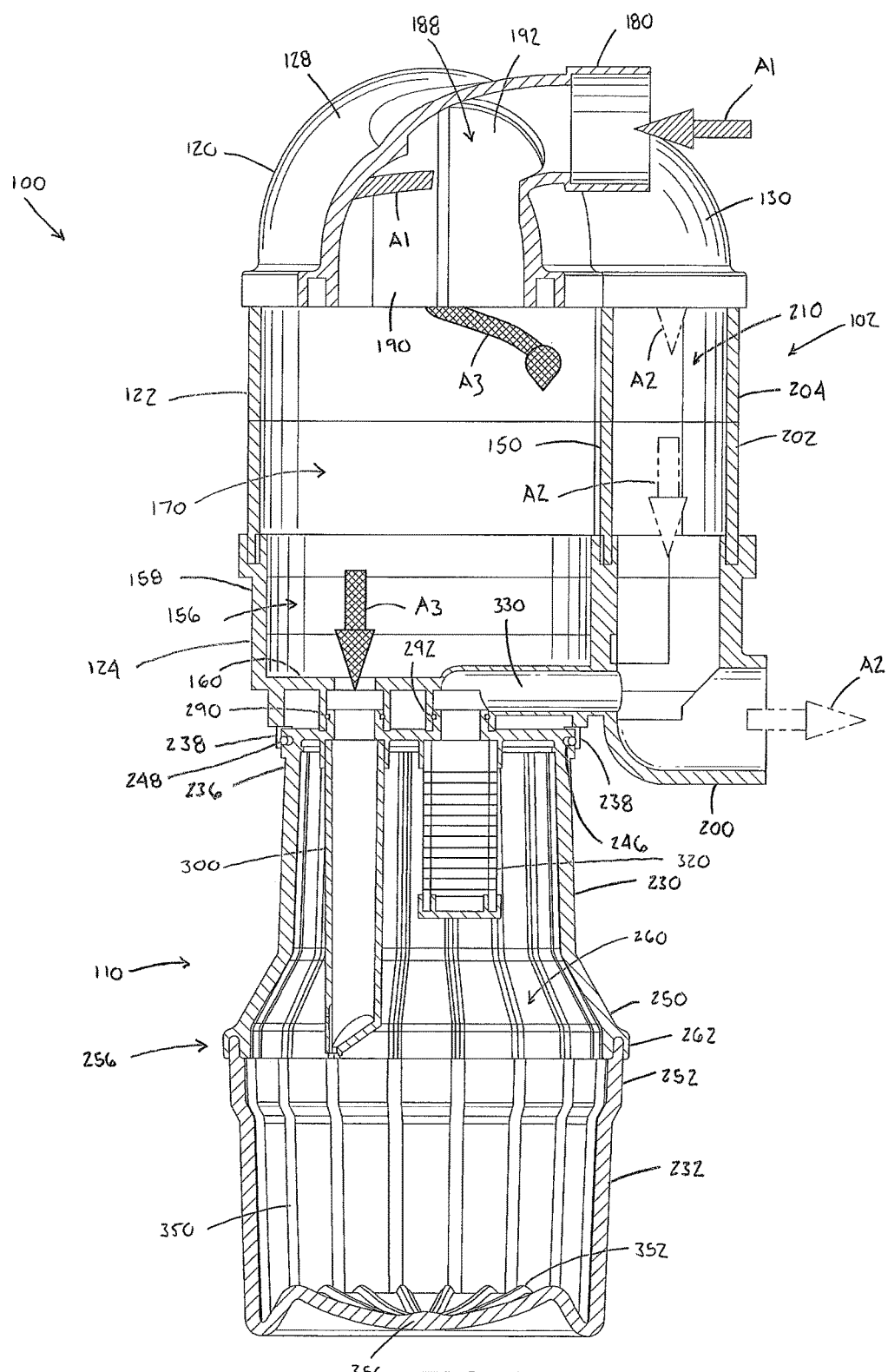
FIG. 3 is a side section view taken through the middle of the apparatus shown in FIG. 1, which also shows the primary flow path of dental office suction effluent drawn into the apparatus.
Figure 4:
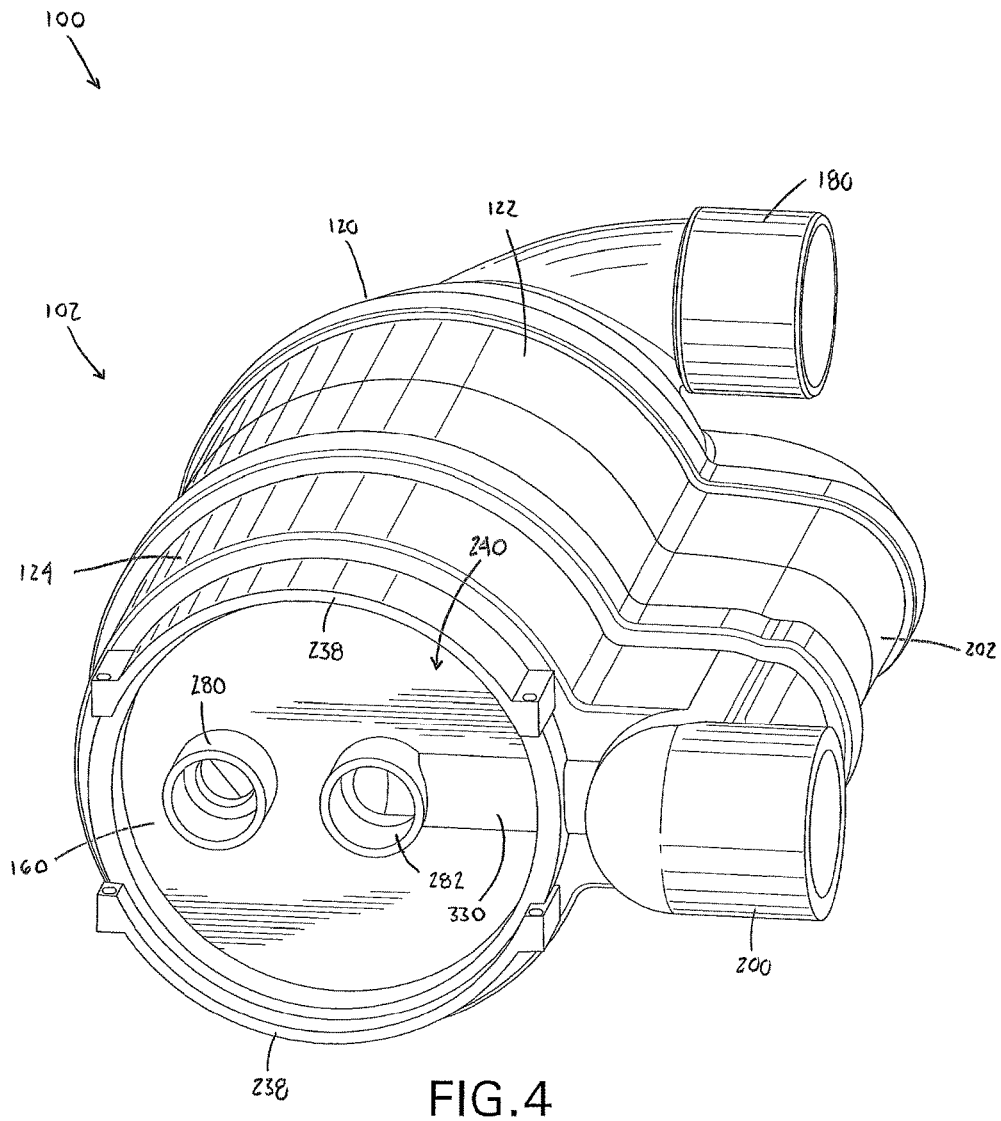
FIG. 4 is a perspective view of an upper chamber of the apparatus shown in FIG. 1, as viewed from the bottom.

With reference to FIGS. 2 and 3, an exit port 186 is provided in the upper portion 120. The exit port 186 can be defined by the second wall portion 130 of the upper portion outer wall 126 together with an internal divider 188 formed in the upper portion 120 to separate the inlet 180 from the exit port 186. As depicted, the divider 188 includes a cylindrical section 190 and a curved section 192 extending from the cylindrical section and into engagement with an interface of the first and second wall portions 128, 130 adjacent the inlet 180. The first wall portion 128 together with the divider 188 define a circular flow path for the dental office suction effluent being drawn into the upper portion 120 of the upper chamber 102. According to one aspect, the exit port 186 is so arranged such that gases of dental office suction effluent entering the upper chamber 102 through the inlet 180 has to change direction by more than at least 50°, and more preferably at least 60°, before the gases can exit the upper chamber 102 through the exit port 186. In FIGS. 1-3, the primary flow of gases through the upper chamber 102 is illustrated using arrows "A2". The dental office suction effluent is permitted to expand as it enters the upper portion 120 of the apparatus 100. The expansion and the change of flow direction in the upper portion 120 help separate gases from liquids and solids of the dental office suction effluent being drawn into the apparatus 100. The divider 188 defines an expansion/deceleration zone within the upper chamber interior volume 170, which further assists in separating liquids and solids from the intake stream.

An outlet 200 is provided in the lower portion 124 for establishing a connection to an outlet line (not shown) in fluid communication with a vacuum pump (not shown). As best shown in FIGS. 1-3, the central portion 122 includes a columnar portion 202 having a longitudinal axis substantially parallel to the longitudinal axis defined by the upper chamber 102. The columnar portion 202 can be defined by an arcuate shaped outer wall 204 and the internal wall portion 150. The columnar portion 202 is further separated from the upper chamber interior volume 170 by the internal wall portion 150 of the central portion 122. The columnar portion 202 is in communication with the exit port 186 and the outlet 200 and cooperates with the upper portion 120 and the lower portion 124 to define a gas conduit 210 for gases of the dental office suction exiting the upper chamber interior volume 170 through the exit port 186 to flow out of the outlet 200.

A flow path for liquids and solids of the dental office suction effluent are illustrated using arrows "A3" in FIGS. 1-3. The liquids and solids of the dental office suction effluent travel along the substantially cylindrical internal wall portion 150 of the central portion 122 of the upper chamber 102 and, predominantly by the force of gravity, flow into the basin portion 156 of the lower portion 124.

The upper portion 120 and the lower portion 124 of the upper chamber 102 can be formed of non-transparent or non-translucent materials. To comply with ISO standards, the central portion 122 is preferably formed of transparent or translucent materials. As depicted in FIG. 2, the central portion 122 is defined by the pair of stacked parts 140, 144, which can be common shaped and sized parts 220. It should be appreciated that more or less than the depicted number of parts 220 can be used to form the central portion 122. For example, a plurality of parts 220 can be formed and joined together intermediate the upper portion 120 and the lower portion 124, if desired. It should be appreciated that the materials utilized for the upper chamber 102 are polymeric in nature, and are joined using conventional methods (e.g., adhesives and/or welding).

Figure 5:
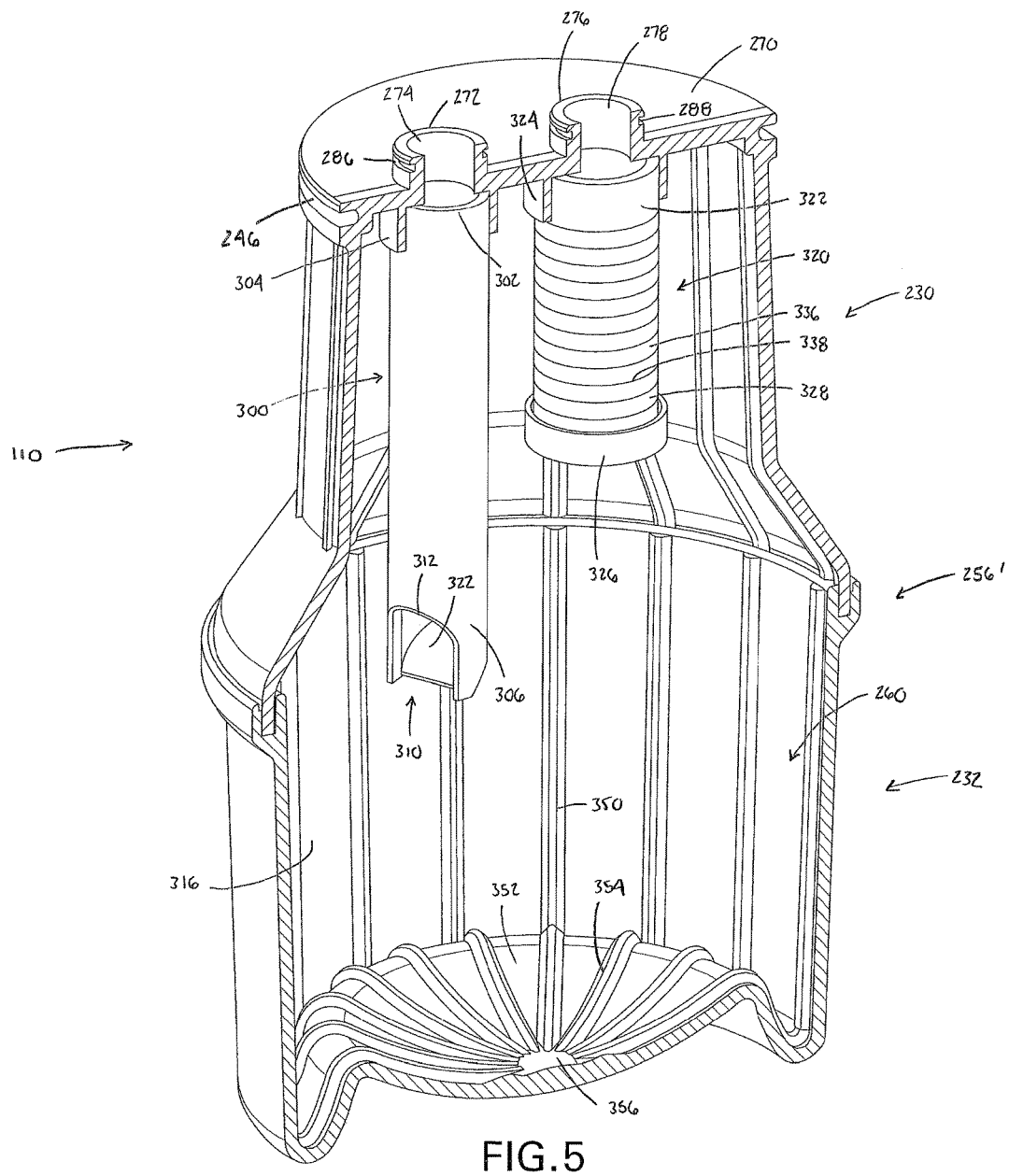
FIG. 5 is a partial section view of a solids collection canister of the apparatus shown in FIG. 1.
Figure 6A:
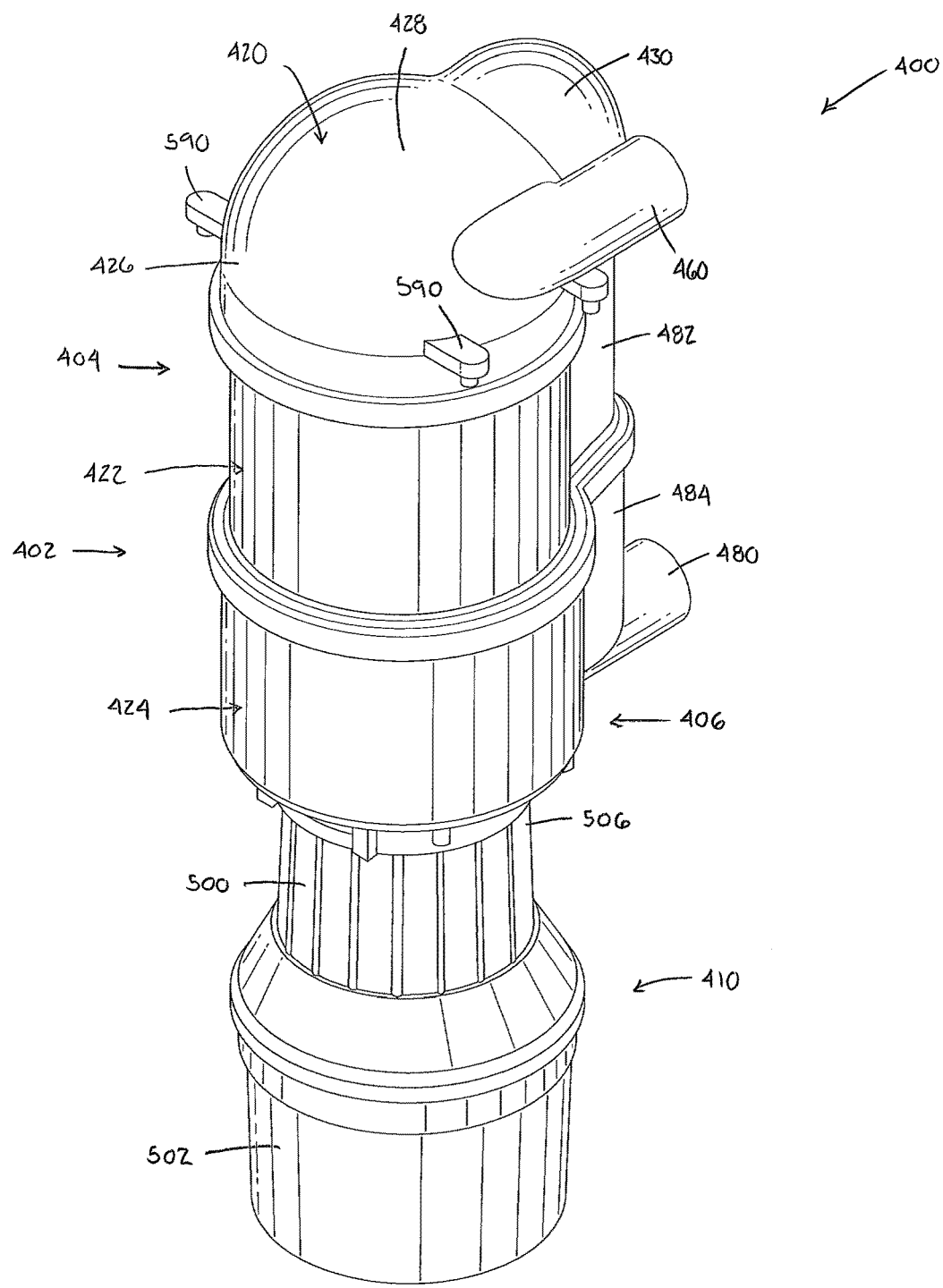
FIGS. 6A-6D are perspective views of another embodiment of an apparatus for removing amalgam and waste particles from dental office suction effluent according to the present invention.
Figure 6B:
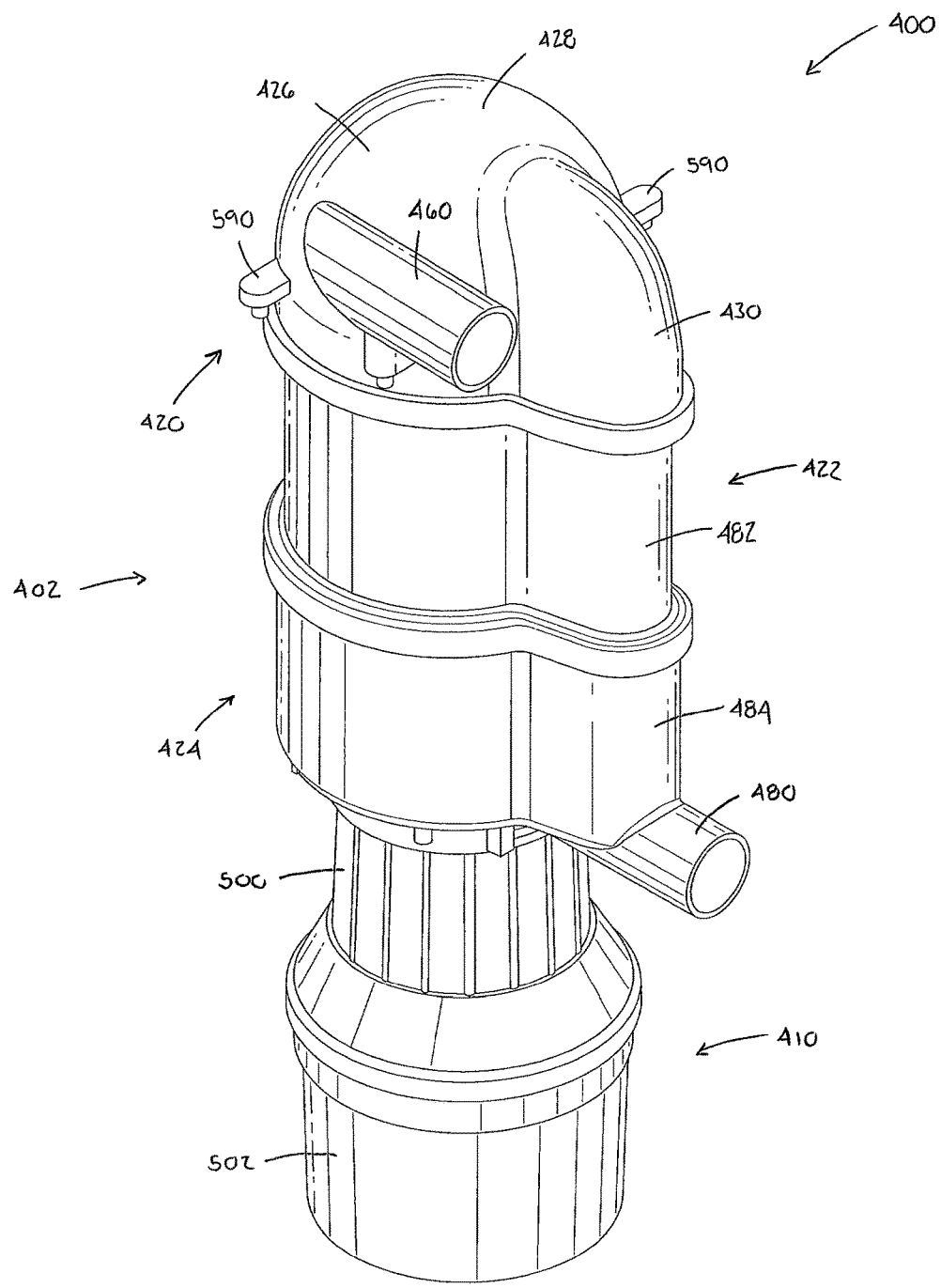
Figure 6C:
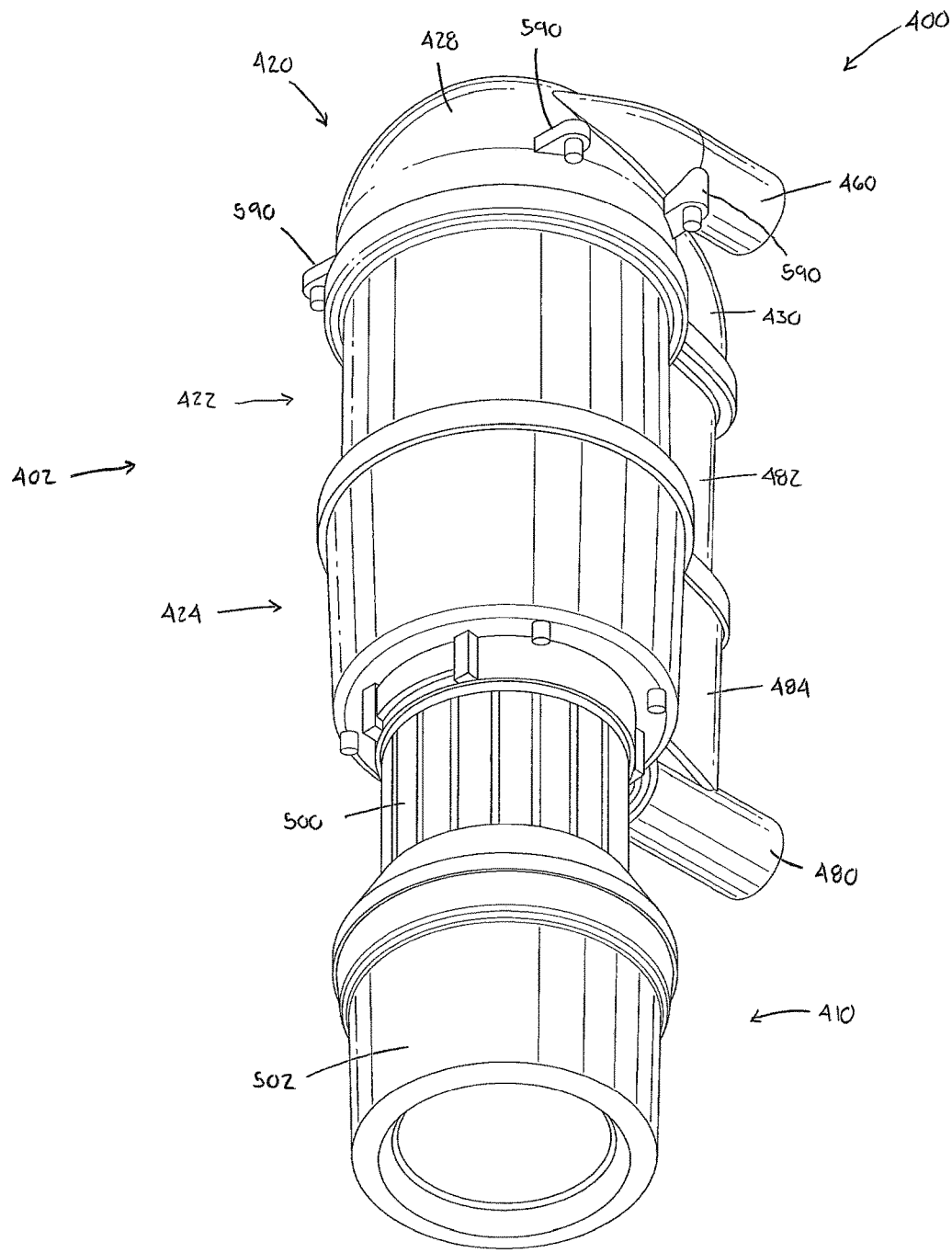
Figure 6D:
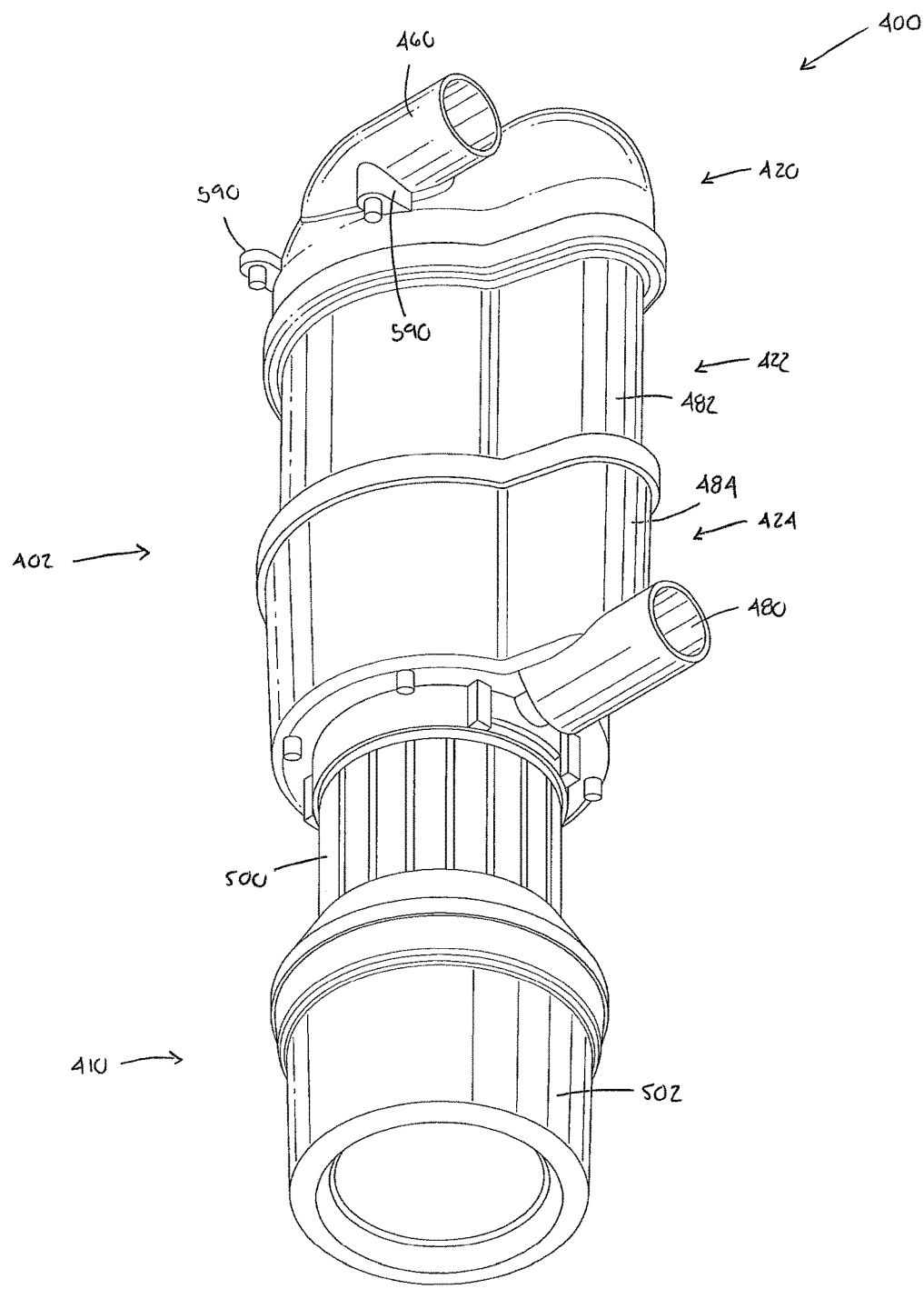

With reference to FIG. 3, the solids collection canister 110 includes a top portion 230 and a bottom portion 232. The bottom portion 232 can have an outer circumference that is greater than an outer circumference of the top portion 230; although, this is not required. The top portion 230 includes and upper end portion 236 releasably secured to the basin portion 156 of the upper chamber lower portion 124. In the depicted embodiment, a pair of circumferentially spaced fastening members 238 which together with the bottom wall 160 of the basin portion 156 define a recess 240 dimensioned to receive the upper end portion 236 (see FIG. 4). Once properly positioned opposed end portions of one fastening member 238 are connected to corresponding end portions of the other fastening member 238 thereby securing the upper end portion 238 of the top portion 230 to the basin portion 156. As best depicted in FIGS. 3 and 5, the upper end portion 236 can include a circumferential groove 246 dimensioned to receive a seal 248 (such as an O-ring) which provides a leak-tight connection between the upper chamber 102 and the solids collection canister 110. Further, to provide for a compact apparatus 100, a longitudinal axis defined by the solids collection canister 110 can be aligned (i.e., coaxial) with the longitudinal axis of the upper chamber 102.

A lower end portion 250 of the top portion 230 is joined to an upper end portion 252 of the bottom portion 232 by a circumferential seam 256 to define a solids collection canister interior volume 260. According to one aspect depicted in FIG. 3, the circumferential seam 256 is defined by a flange 262 located on the lower end portion 250 overlapping the upper end portion 252, which is located on the outside of the lower end portion 250. An adhesive can be applied to the circumferential seam 256 (to define a glue joint) to permanently affix the top and bottom portions 230, 232 of the solids collection canister 110. FIG. 5 illustrates an alternative configuration for the circumferential seam 256' between the top portion 230 and the bottom portion 232. It will be appreciated that other seam techniques could be utilized without departing from the invention.

As perhaps best illustrated in FIG. 5, the top portion 230 of the solids collection canister 110 is provided with top wall 270 including a first projection 272 having a first opening 274 and a second projection 276 having a second opening 278. The first opening 274 communicates with a drain 280 provided in the bottom wall 160 of the basin portion 156 of the upper chamber 102 (see FIG. 4). The second opening 278 communicates with an inlet port 282 (which communicates with the outlet 200) also provided in the bottom wall 160 of the basin portion 156 (see FIG. 4). In the assembled condition of the apparatus 100, the first projection 272 is received in the drain 280 and the second projection 276 is received in the inlet port 282. To provide for a sealed connection between these components, each of the first and second projections 272, 276 includes a respective circumferential groove 286, 288 for receiving a respective seal (i.e., O-ring) 290, 292 (see FIG. 3).

The solids collection canister 110 further comprises a riser 300 that conveys liquids and solids of the dental office suction effluent flowing from the upper chamber interior volume 170 through the drain 280 and the first opening 274 to the bottom portion 232 of the solids collection canister (see FIG. 5). According to one embodiment, the riser 300 is an elongated cylindrical shaped member having a longitudinal axis substantially parallel to the longitudinal axis of the solids collection canister 110. According to one aspect, an upper end 302 of the riser 300 is secured in a boss 304 depending from the top wall 270 of the top portion 230, the boss 304 having an axis that is coincident with an axis of the drain 280. A lower end 306 of the riser 300 includes a tip portion 310 having an exit opening 312. The tip portion 310 is shaped and configured to direct liquids and solids of the dental office suction effluent conveyed thereby toward an inner wall 316 of the bottom portion 232 of the solids collection canister 110. According to one aspect, the tip portion 310 includes an inner surface 322 canted upwardly toward the top wall 270 which directs liquids and solids of the dental office suction effluent away from a flow restrictor 320.

As noted, the solids collection canister 110 further includes the flow restrictor 320, which is mounted to and depends from the top wall 270 of the top portion 230. According to one aspect, the flow restrictor has an upper end 322 secured in a second boss 324 depending from the top wall 270, the second boss 324 having an axis that is coincident with an axis of the inlet port 282. A cap 326 can be secured to a lower end 328 of the flow restrictor 320. The flow restrictor 320 is in fluid communication with the outlet 200 via the second opening 278 in the top portion 230 and a lower conduit 330 formed in the basin portion 156 of the lower portion 124 of the upper chamber 102 (see FIGS. 3 and 4). The lower conduit 330 is in communication with the inlet port 282 and the outlet 200 and extends in a direction substantially perpendicular to the longitudinal axis of the upper chamber 102. The flow restrictor 320 allows liquids and gases of the dental office suction effluent to exit the solids collection canister interior volume 260, but prohibits solids of the dental office suction effluent from exiting the solids collection canister interior volume 260. This can be accomplished through the use of a tubular element 336, which is provided with circumferential slits 338 dimensioned to prevent the passage of solids larger than a predetermined size. Within the flow restrictor 320, a porous material (not shown) can be provided (e.g., sand media), which allows the passage of liquids and gases, but does not allow for the passage of solids.

With reference to FIG. 5, the inner wall 316 of the bottom portion 232 of the solids collection canister 110 can be provided with a plurality of upwardly extending flutes 350. Similarly, a bottom wall 352 of the bottom portion 232 can be provided with a plurality of flutes 354, which can be contiguous with the flutes 350. The flutes 350, 354 provide strength and also enhance separation of solids from liquids. The bottom wall 352 of the solids collection canister 110 can further include an indentation or punt 356, which encourages solids of the dental office suction effluent to settle initially along a perimeter of the solids collection canister interior volume 260. The punt 356 also makes it easy to hold and maintain the solids collection canister 110 in position with one hand with respect to the upper chamber 102 during removal and replacement operations.

As indicated previously, in the depicted embodiment, the bottom portion 232 of the solids collection canister 110 has an outer circumference that is greater than the outer circumference of the top portion 232. This allows the solids collection canister 110 to collect a larger volume (e.g., 1.5 L) of solids of the dental office suction effluent than could otherwise be collected if the dimensions were the same or if the bottom portion 232 was smaller than the top portion 230. This configuration can be utilized as a replacement for solids collection receptacles on known amalgam separators, such as the HG5® unit presently being sold by SolmeteX, Inc., which only are able to collect 1.0 L of solids. This reduces the frequency of canister changes. An outer ribbing 360 can also be provided on the solids collection canister 110 to improve its strength and also the ease by which it can be gripped (see FIG. 1). It should be appreciated that the solids collection canister 110 can be replaced once a predetermined volume (e.g., 1.5 L) of solids has been collected therein.

FIG. 6A through FIG. 9 depict another embodiment of an apparatus 400 for removing amalgam and waste particles from dental office suction effluent according to the present invention. The apparatus 400 has the same functionality and defines the same flow paths as the apparatus 100 shown in FIGS. 1-5, but includes additional features, which are discussed in greater detail below.

As shown in FIGS. 6A-6D, the apparatus 400 generally comprises an upper chamber 402 having an upper end 404 and a lower end 406, and a solids collection canister 410 removably secured to the lower end of the upper chamber. The upper chamber includes an upper portion 420, a central portion 422, and a lower portion 424. The upper portion 420 includes an outer wall portion 426 having a first wall portion 428 and a second wall portion 430 projecting outwardly from the first wall portion 128. According to one aspect, the first wall portion 428 can be substantially hemispherical dome-shaped; although, this is not required.

Figure 7:
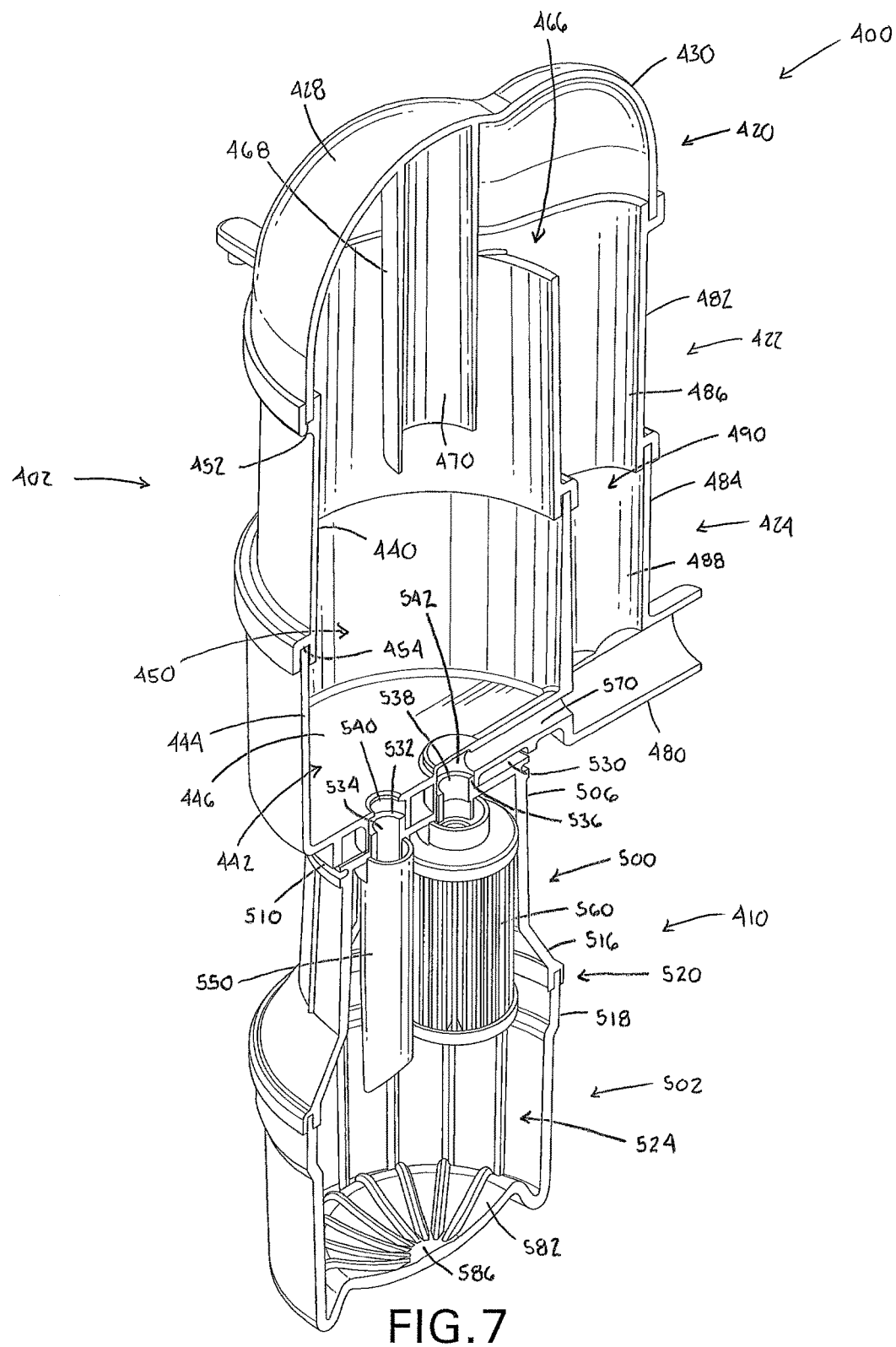
FIG. 7 is a partial section view of the apparatus shown in FIG. 6B.
Figure 9:
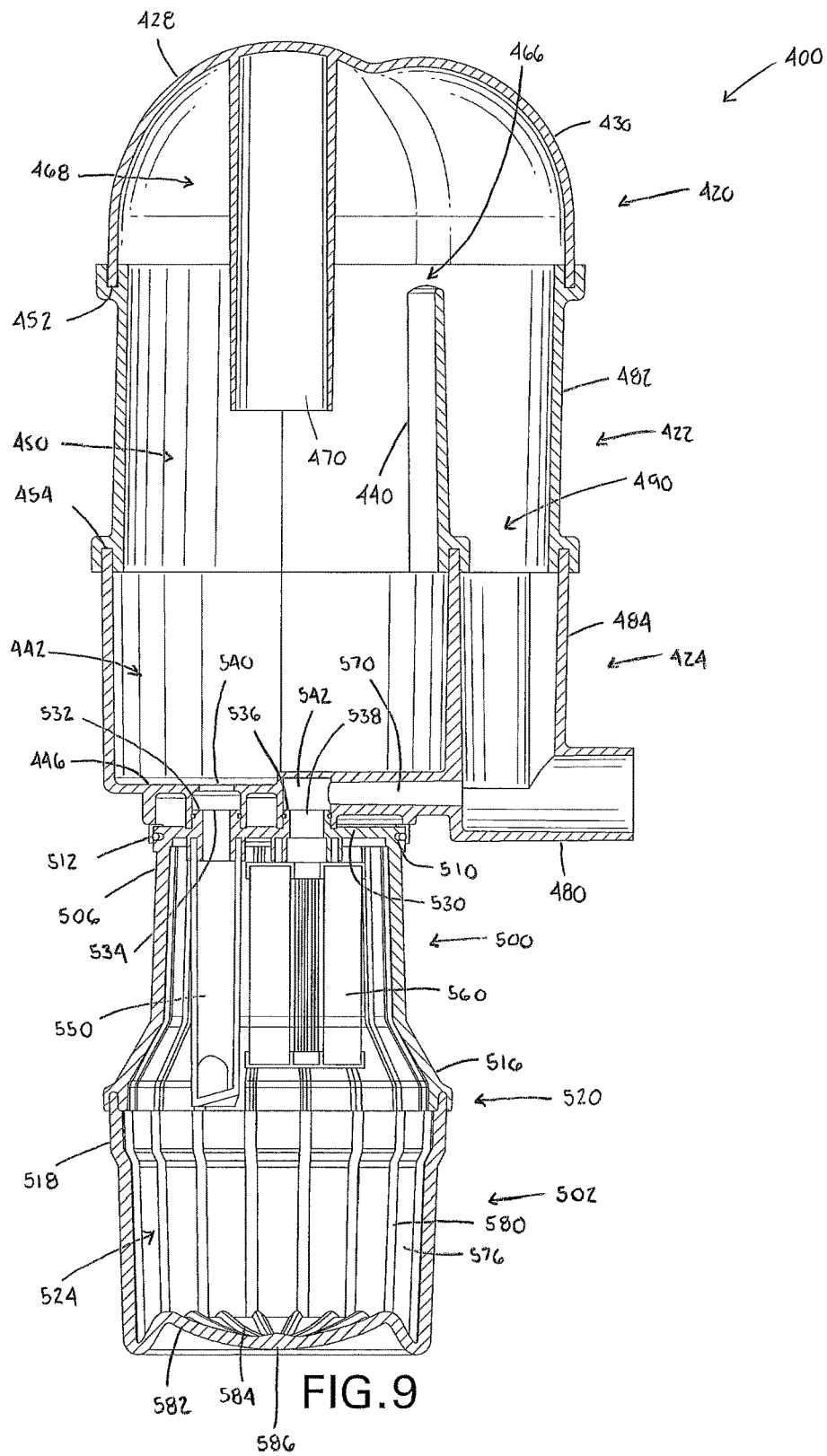
FIG. 9 is a section view of the apparatus shown in FIG. 6B.

With particular reference to FIGS. 7 and 9, the central portion 422 includes a substantially cylindrical internal wall portion 440 adapted to impart a circular flow to the dental office suction effluent being drawn into the upper chamber 402. The lower portion 424 of the upper chamber 402 includes a basin portion 442. The basin portion 442 is defined by a vertical wall 444 and a bottom wall 446. The upper portion 420, the substantially cylindrical internal wall portion 440 of the central portion 422 and the basin portion 446 of the lower portion 424 cooperate to define an upper chamber interior volume 450.

The upper portion 420 and the lower portion 424 of the upper chamber 402 can be formed of non-transparent or non-translucent materials. To comply with ISO standards, the central portion 422 is preferably formed of transparent or translucent materials. It should be appreciated that the materials utilized for the upper chamber 402 are polymeric in nature, and can be joined using conventional methods (e.g., adhesives and/or welding). For example, as best depicted in FIGS. 7 and 9, one manner for connecting the upper portion 420 to the central portion 422 and the central portion 422 to the lower portion 424 is to form grooves 452, 454 at the peripheral edges of the central portion 422, which receive straight peripheral edges of the upper and lower portions, respectively. This configuration improves the moldability of the parts, and ensures an accurate seal between the portions 420, 422, 424 that comprise the upper chamber 402.

An inlet 460 is provided in the upper portion 420 of the upper chamber 402 for establishing a connection to an inlet line (not shown) in fluid communication with at least one dental suction wand (not shown). The inlet 460 is configured such that dental office suction effluent drawn through the at least one dental suction wand enters the upper portion 420 of the upper chamber 402 along an initial lateral flow path into the upper portion 420 and then a circular flow path through the upper portion 420 above the internal wall portion 440 of the central portion 422. Again, it should be appreciated that the use of the substantially hemispherical domed-shaped first wall portion 428 of the upper portion outer wall 426 allows the incoming dental office suction effluent to quickly change direction as it enters the upper portion 420 of the apparatus 400.

Figure 8:
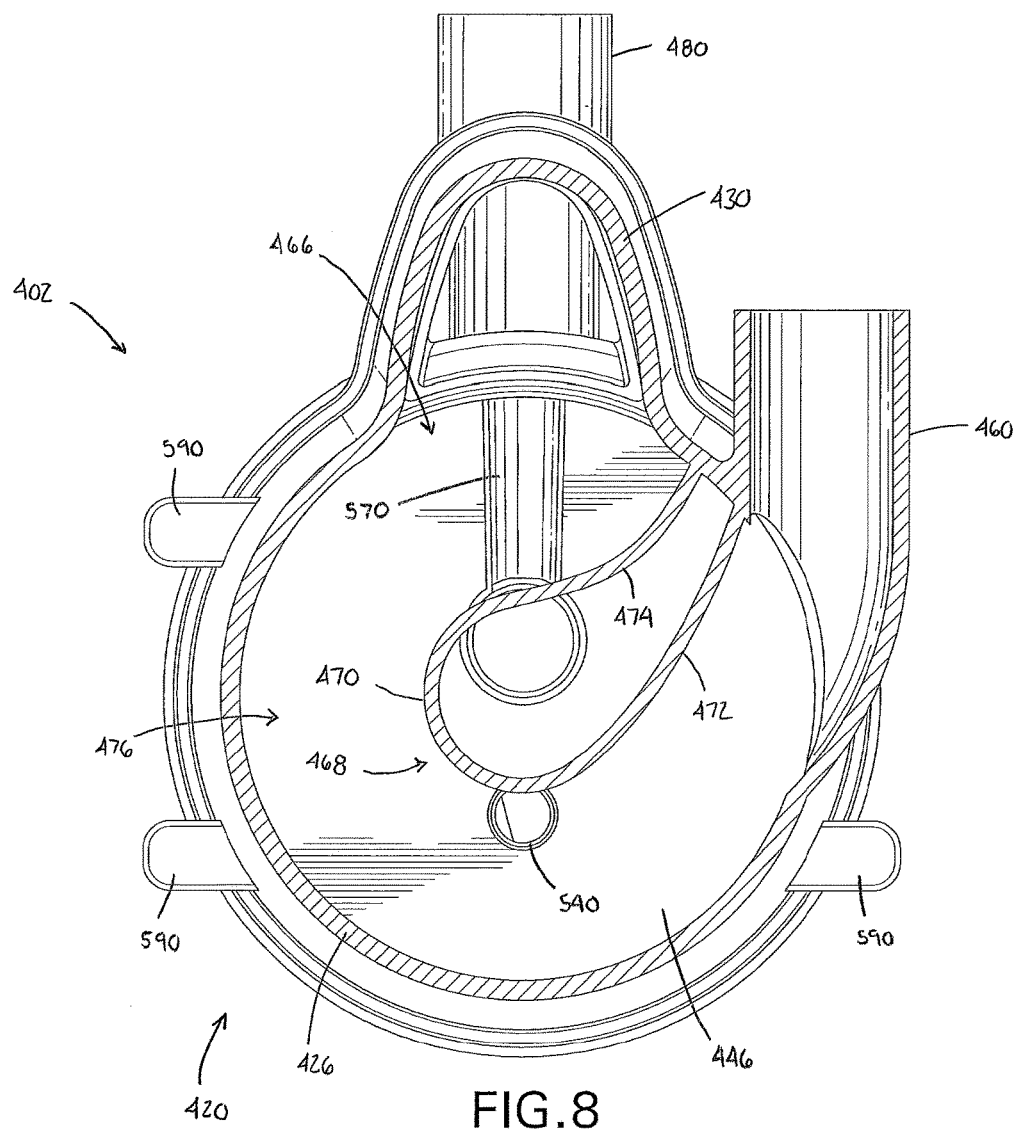
FIG. 8 is a section view through an upper portion of an upper chamber of the apparatus shown in FIG. 6A.

With reference to FIGS. 7-9, an exit port 466 is provided in the upper portion 420. The exit port 466 can be defined by the second wall portion 430 of the upper portion 420 together with an internal divider 468 formed in the upper portion 420 to separate the inlet 460 from the exit port 466. As depicted, the divider 468 includes a cylindrical section 470 and a pair of curved sections 472, 474 extending from the cylindrical section and into engagement with an interface of the first and second wall portions 428, 430 adjacent the inlet 460. The first wall portion 428 together with the divider 468 define a circular flow path for the dental office suction effluent being drawn into the upper portion 420 of the upper chamber 402. According to one aspect, the exit port 466 is so arranged such that gases of dental office suction effluent entering the upper chamber 402 through the inlet 460 has to change direction by more than at least 50°, and more preferably at least 60°, before gases can exit the upper chamber 402 through the exit port 466. The dental office suction effluent is permitted to expand as it enters the upper portion 420 of the apparatus 400. The expansion and the change of flow direction help separate gases from liquids and solids of the dental office suction effluent. The divider 468 defines an expansion/deceleration zone 476 within the upper chamber interior volume 450, which further assists in separating liquids and solids from the intake stream (see FIG. 7).

An outlet 480 is provided in the lower portion 424 for establishing a connection to an outlet line (not shown) in fluid communication with a vacuum pump (not shown). The central portion 422 includes a columnar portion 482 and the lower portion 426 includes a corresponding columnar portion 484. Each columnar portion 482, 484 has a longitudinal axis substantially parallel to a longitudinal axis defined by the upper chamber 402. As best depicted in FIGS. 7 and 9, the columnar portion 482 can be defined by an arcuate shaped outer wall 486 and the internal wall portion 440, which separates the columnar portion 482 from the upper chamber interior volume 450. The columnar portion 484 can be defined by an arcuate shaped outer wall 488 and the wall 444 of the basin portion 442. Each columnar portion 482, 484 is in communication with the exit port 466 and the outlet 480 and cooperates with the upper portion 420 and the lower portion 424 to define a gas conduit 490 for gases of the dental office suction exiting the interior volume 450 through the exit port 466 to flow out of the outlet 480. Similar to the function of the apparatus 100, liquids and solids of the dental office suction effluent travel along the substantially cylindrical internal wall portion 440 of the central portion 422 of the upper chamber 402 and, predominantly by the force of gravity, flow into the basin portion 446 of the lower portion 424.

With reference to FIGS. 6A-6D, the solids collection canister 410 includes a top portion 500 and a bottom portion 502. The bottom portion 502 can have an outer circumference that is greater than an outer circumference of the top portion 500; although, this is not required. The top portion 500 includes and upper end portion 506 releasably secured to the basin portion 442 of the upper chamber lower portion 424. As best depicted in FIGS. 7 and 9, the upper end portion 506 can include a circumferential groove 510 dimensioned to receive a seal 512 (such as an O-ring) which provides a leak-tight connection between the upper chamber 402 and the solids collection canister 410. To provide for a compact apparatus 400, a longitudinal axis defined by the solids collection canister 410 can be aligned (i.e., coaxial) with the longitudinal axis of the upper chamber 402. A lower end portion 516 of the top portion 230 is joined to an upper end portion 518 of the bottom portion 502 by a circumferential seam 520 to define a solids collection canister interior volume 524. An adhesive can be applied to the circumferential seam 520 to permanently affix the top and bottom portions 500, 502. Again, it will be appreciated that other seam techniques could be utilized without departing from the invention.

With continued reference to FIGS. 7 and 9, the top portion 500 of the solids collection canister 410 is provided with top wall 530 including a first projection 532 having a first opening 534 and a second projection 536 having a second opening 538. The first opening 534 communicates with a drain 540 provided in the bottom wall 446 of the basin portion 442 of the upper chamber 402. The second opening 538 communicates with an inlet port 542 also provided in the bottom wall 446 of the basin portion 442. In the assembled condition of the apparatus 400, the first projection 532 is received in the drain 540 and the second projection 536 is received in the inlet port 542. To provide for a sealed connection, each of the first and second projections 532, 536 can include a circumferential groove for receiving a seal (i.e., O-ring) (see FIG. 9).

The solids collection canister 410 further comprises a riser 550 mount to and depending from the top wall 446 that conveys liquids and solids of the dental office suction effluent flowing from the upper chamber interior volume 450 through the drain 540 and the first opening 534 to the bottom portion 502 of the solids collection canister 410. The riser 550 is shaped and configured similar to riser 300, and the manner for securing the riser 550 to the top wall 446 is similar to the connection of the riser 300 to the top wall 270. Therefore, further description of these features of the apparatus 400 is omitted for conciseness.

A flow restrictor 560 is mounted to and depends from the top wall 446. Because the manner for securing the flow restrictor 560 to the top wall 446 is similar to the connection of the flow restrictor 320 to the top wall 270, further description of these features of the apparatus 400 will be omitted for conciseness. The flow restrictor 560 is in fluid communication with the outlet 480 via the second opening 538 in the top portion 500 and a lower conduit 570 formed in the basin portion 442 of the lower portion 424 of the upper chamber 402 (see FIGS. 7 and 9). The lower conduit 570 is in communication with the inlet port 542 and the outlet 480 and extends in a direction substantially perpendicular to the longitudinal axis of the upper chamber 402. The flow restrictor 560 allows liquids and gases of the dental office suction effluent to exit the solids collection canister interior volume 524, but prohibits solids of the dental office suction effluent from exiting the solids collection canister interior volume 524.

In the depicted embodiment, the flow restrictor 560 can be formed of an inert micro-fiberglass material bonded with a stable resin, randomly set into a multi-layer composite. In the present embodiment of the invention, the material of the flow restrictor 560 has a 3 micron absolute rating. In the illustrated flow restrictor 560, the fiberglass material is co-pleated with inner and outer support layers, which can be made of corrosion resistant materials such as metal (stainless steel) and/or plastic. It is important that the material, at gravity feed, have a low pressure differential across the separation media. Use of a flow restrictor having a configuration as described should improve the separation efficiency of the amalgam separator apparatus 400 substantially, with amalgam particle separation efficiencies of 99% or greater being expected in accordance with testing under the ISO 11143:2008 standard.

With reference to FIG. 9, an inner wall 576 of the bottom portion 502 of the solids collection canister 410 can be provided with a plurality of upwardly extending flutes 580. Similarly, a bottom wall 582 of the bottom portion 502 can be provided with a plurality of flutes 584, which can be contiguous with the flutes 580. The flutes 580, 584 provide strength and also enhance separation of solids from liquids. The bottom wall 582 of the solids collection canister 410 can further include an indentation or punt 586, which encourages solids of the dental office suction effluent to settle initially along a perimeter of the solids collection canister interior volume 524.

FIG. 8 depicts mounts 590, which are formed in the upper portion 420. The mounts 590 can be connected to brackets or hardware (not shown) allowing the upper chamber 402 to be fixedly mounted to a wall or other location. It will be appreciated that the location and configuration of the mounts 590 is not per se critical, and that a variety of different mounting arrangements could be used.

In its broadest sense, an exemplary method for removing amalgam and waste particles from dental office suction effluent comprises providing an apparatus as disclosed herein, and suctioning waste from a patient's mouth through a dental office suction effluent wand in fluid communication with the apparatus. Once the interior volume of the solids collection canister has been sufficiently filled with solid particles (e.g., 1.5 L), the entire solids collection canister is removed from the upper chamber, and a new solids collection canister is secured to the upper chamber in its place. The solids collection canister filled with collected solids can be packed and shipped to a recycling facility, where the metals are recovered.

According to one aspect, a method for removing amalgam and waste particles from dental office suction effluent comprises imparting a circular flow path to a dental office suction effluent entering an upper separation chamber of a separation apparatus; separating gases from the dental office suction effluent and discharging the separated gases from the upper separation chamber; directing the dental office suction effluent into a solids collection canister removably secured to a lower end of the upper chamber via a riser located in the solids collection canister; separating solids from the dental office suction effluent in the solids collection canister; and discharging liquids and gases of the dental office suction effluent through a flow restrictor located in the solids collection canister. The method can further comprise discharging the separated gases through a separate gas conduit provided in the upper chamber. The method can further comprise conveying liquids and solids of the dental office suction effluent flowing from the upper chamber toward an inner wall of the solids collection canister.

The device and method are preferably capable of handling an effluent flow rate of at least one 1 L per minute. The flow rate of effluent is primarily governed by the flow restrictor. The amount of effluent flowing into the device will vary depending upon the number of chairs in use. When the effluent inflow temporarily exceeds the maximum flow rate, the effluent will accumulate in the upper chamber, and then gradually drain off through the solids collection canister when inflow rates diminish. Thus, the device can be used in conjunction with multiple dental chairs simultaneously.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. An apparatus for removing amalgam and waste particles from dental office suction effluent, the apparatus comprising:
    an upper chamber having an upper end and a lower end, the upper chamber including an upper portion, a central portion having a substantially cylindrical internal wall portion, and a lower portion having a basin portion, wherein the upper portion, the central portion and the basin portion of the lower portion cooperate to define an upper chamber interior volume;
    an inlet provided in the upper portion of the upper chamber for establishing a connection to an inlet line in fluid communication with at least one dental suction wand, and an outlet provided in the lower portion of the upper chamber for establishing a connection to an outlet line in fluid communication with a vacuum pump;
    a solids collection canister removably secured to the lower end of the upper chamber, the solids collection canister including a top portion and a bottom portion which together define a solids collection canister interior volume, the top portion of the solids collection canister being provided with a first opening and a second opening, the first opening communicating with a drain provided in the basin portion of the upper chamber, the second opening communicating with the outlet;
    a riser communicating with the first opening, the riser adapted to convey liquids and solids of the dental office suction effluent flowing from the upper chamber interior volume through the drain and the first opening to the bottom portion of the solids collection canister; and
    a flow restrictor communicating with the second opening and adapted to allow liquids and gases of the dental office suction effluent to exit the solids collection canister interior volume but prohibit solids of the dental office suction effluent from exiting the solids collection canister interior volume.

2. The apparatus of claim 1, wherein the inlet is shaped and configured such that dental office suction effluent drawn through the at least one dental suction wand enters the upper chamber along a lateral flow path above the substantially cylindrical internal wall portion of the central portion, the lateral flow path being substantially perpendicular to a longitudinal axis defined by the upper chamber.

3. The apparatus of claim 2, wherein the substantially cylindrical internal wall portion of the central portion is adapted to impart a circular flow path to the dental office suction effluent.

4. The apparatus of claim 1, wherein an exit port is provided in the upper portion, the exit port being arranged such that a flow of gases of dental office suction effluent entering the upper chamber through the inlet changes direction by more than 60° before the gases exit the upper chamber through the exit port.

5. The apparatus of claim 4, wherein the central portion includes a columnar portion having a longitudinal axis substantially parallel to a longitudinal axis defined by the upper chamber, the columnar portion being separated from the upper chamber interior volume by the internal wall portion, the columnar portion cooperating with the upper portion and the lower portion to define a gas conduit for gases exiting the upper chamber interior volume through the exit port to flow out of the outlet.

6. The apparatus of claim 4, wherein a divider is located in the upper portion of the upper chamber to separate the inlet from the exit port, the divider defining an expansion zone within the upper chamber interior volume.

7. The apparatus of claim 1, wherein the riser includes a tip portion having an exit opening, the tip portion being adapted to direct liquids and solids of dental office suction effluent conveyed thereby toward an inner wall of the bottom portion of the solids collection canister.

8. The apparatus of claim 7, wherein the tip portion includes a surface canted upwardly toward the top portion of the solids collection canister.

9. The apparatus of claim 1, wherein the flow restrictor is mounted to and depends from the top portion solids collection canister, the flow restrictor being in fluid communication with the outlet.

10. The apparatus of claim 9, wherein a lower conduit is formed in the lower portion of the upper chamber, the lower conduit being in fluid communication with the second opening and the flow restrictor.

11. The apparatus of claim 1, wherein the top portion and the bottom portion of the solids collection canister are joined together by a circumferential seam.

12. The apparatus of claim 1, wherein the bottom portion of the solids collection canister has an outer circumference that is greater than an outer circumference of the top portion of the solids collection canister.

13. An apparatus for removing amalgam and waste particles from dental office suction effluent, the apparatus comprising:
an upper chamber having an upper end, a lower end and a basin portion, the upper chamber defining a longitudinal axis; and
a solids collection canister removably secured to the lower end of the upper chamber, the solids collection canister including a top portion provided with a first opening and a second opening, the first opening communicating with a drain provided in the basin portion of the upper chamber;
an inlet provided in the upper chamber for establishing a connection to an inlet line in fluid communication with at least one dental suction wand, the inlet being shaped and configured such that dental office suction effluent enters the upper chamber along a lateral flow path which is substantially perpendicular to the longitudinal axis of the upper chamber;
an outlet provided in the upper chamber for establishing a connection to an outlet line in fluid communication with a vacuum pump;
an exit port provided in the upper chamber and communicating with the outlet, the exit port discharging gases of dental office suction effluent entering the upper chamber through the inlet;
a separate gas conduit provided in the upper chamber and having a longitudinal axis substantially parallel to the longitudinal axis of the upper chamber, the gas conduit communicating with the exit port and the outlet for directing the discharged gases toward the outlet;
a flow restrictor located in the solids collection canister and adapted to allow liquids and gases of the dental office suction effluent to exit the solids collection canister but prohibit at least about 99% by weight of solids of the dental office suction effluent that enter the solid collection canister from exiting the solids collection canister.

14. The apparatus of claim 13, wherein the flow restrictor is in fluid communication with the exit port via the second opening in the solids collection canister and a lower conduit formed in the basin portion of the upper chamber.

15. The apparatus of claim 13, wherein the flow restrictor is formed of an inert micro-fiberglass material bonded with a stable resin, randomly set into a multi-layer composite.

16. The apparatus of claim 13, wherein the upper chamber includes a substantially cylindrical internal wall portion adapted to impart a circular flow path to the dental office suction effluent, the internal wall portion at least partially defining the gas conduit.

17. The apparatus of claim 13, further including a riser communicating with the first opening, the riser adapted to convey liquids and solids of dental office suction effluent flowing from the upper chamber interior volume through the drain and the first opening to a bottom portion of the solids collection canister.

18. A method for removing amalgam and waste particles from dental office suction effluent, the method comprising:
imparting a circular flow path to a dental office suction effluent entering an upper separation chamber of a separation apparatus
separating gases from the dental office suction effluent and discharging the separated gases from the upper separation chamber;
directing the dental office suction effluent into a solids collection canister removably secured to a lower end of the upper chamber via a riser located in the solids collection canister;
separating solids from the dental office suction effluent in the solids collection canister; and
discharging liquids and gases of the dental office suction effluent through a flow restrictor located in the solids collection canister.

19. The method of claim 18, further including discharging the separated gases through a separate gas conduit provided in the upper chamber.

20. The method of claim 18, further including conveying liquids and solids of the dental office suction effluent flowing from the upper chamber toward an inner wall of the solids collection canister.

21. In an apparatus for removing amalgam and waste particles from dental office suction effluent that includes a solids collection canister having an interior volume and a flow restrictor in communication with the interior volume of the solids collection canister that is adapted to allow liquids and gases of the dental office suction effluent to exit the solids collection canister interior volume but prohibit solids of the dental office suction effluent from exiting the solids collection canister interior volume, the improvement comprising that the flow restrictor is formed of an inert micro-fiberglass material bonded with a stable resin, randomly set into a multi-layer composite.

* * * * *